(12) United States Patent
Navarro et al.

(10) Patent No.: US 7,563,469 B1
(45) Date of Patent: Jul. 21, 2009

(54) METHOD OF AERATING YEAST PRIOR TO PITCHING

(75) Inventors: Alfonso Navarro, Milwaukee, WI (US); Jeffrey F. Fehring, West Bend, WI (US); Michael C. Barney, Elm Grove, WI (US); David S. Ryder, Mequon, WI (US)

(73) Assignee: Millercoors LLC, Wilmington, DE (US)

( * ) Notice: Subject to any disclaimer, the term of this patent is extended or adjusted under 35 U.S.C. 154(b) by 0 days.

(21) Appl. No.: 09/525,892

(22) Filed: Mar. 15, 2000

(51) Int. Cl.
*C12N 1/16* (2006.01)
(52) U.S. Cl. .......................................... 426/62; 426/29
(58) Field of Classification Search .................... 426/7, 426/13, 11, 16, 15, 60
See application file for complete search history.

(56) References Cited

U.S. PATENT DOCUMENTS

| | | | |
|---|---|---|---|
| 899,756 | A | 9/1908 | Nathan et al. |
| 1,041,298 | A | 10/1912 | Kiefer |
| 1,461,808 | A * | 7/1923 | Snelling ............... 426/48 |
| 1,676,437 | A | 7/1928 | Harrison |
| 2,121,458 | A | 6/1938 | Vogelbusch |
| 2,842,442 | A | 7/1958 | Jeffreys |
| 3,032,476 | A | 5/1962 | Sher |
| 3,164,472 | A | 1/1965 | Stone |
| 4,001,435 | A * | 1/1977 | Hirao et al. ............... 426/3 |
| 4,329,433 | A * | 5/1982 | Seebeck et al. ........... 435/255 |
| 4,348,483 | A | 9/1982 | Skogerson |
| 4,666,718 | A | 5/1987 | Lowery et al. |
| 4,840,802 | A | 6/1989 | Lindberg et al. |
| 5,266,337 | A | 11/1993 | Barwald |
| 5,294,450 | A | 3/1994 | Word et al. |
| 6,265,000 | B1 * | 7/2001 | Shimamura et al. .......... 426/16 |

FOREIGN PATENT DOCUMENTS

| | | |
|---|---|---|
| BE | 1010885 A3 | 2/1999 |
| DE | 202 892 A | 10/1983 |
| EP | 0 218 472 A2 | 4/1987 |
| EP | 0 393 268 A1 | 10/1990 |
| EP | 0 440 975 A2 | 8/1991 |
| GB | 2197341 A | 5/1988 |
| RU | 2092560 C1 | 10/1997 |
| SU | 592843 A | 3/1978 |
| SU | 1296579 A | 3/1987 |

OTHER PUBLICATIONS

Edited by: William A. Hardwick, Handbook of Brewing, 1995, Marcel Dekker, Inc., 181-184, 194-195, and 215-217.*

* cited by examiner

*Primary Examiner*—Jennifer McNeil
*Assistant Examiner*—Jyoti Chawla
(74) *Attorney, Agent, or Firm*—Quarles & Brady, LLP

(57) ABSTRACT

Disclosed is a method of efficiently aerating yeast prior to pitching. In the method, yeast are aerated in an aqueous sugar solution containing zinc.

7 Claims, No Drawings

METHOD OF AERATING YEAST PRIOR TO PITCHING

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Brewer's yeast is used as a biocatalyst to ferment carbohydrates to ethanol in the production of beer and other fermented beverages. In brewing, fermentation is performed by mixing brewer's yeast with wort and incubating the mixture under conditions suitable for fermentation. Wort includes a source of carbohydrates prepared by hot water enzymatic conversion of complex sugars to fermentable sugars in malted grain and adjunct grains. After extraction the wort is boiled to complete extraction, stop enzymatic reactions, and to boil off undesirable compounds. Following boiling the wort is cooled and brewer's yeast is added.

During the brewing process, measuring the specific gravity over time monitors fermentation. The specific gravity declines over the course of fermentation due to a decrease in fermentable carbohydrates and an increase in ethanol concentration. What constitutes an acceptable final specific gravity depends on the type of beer being brewed.

An unacceptably high specific gravity may be caused by a variety of factors, including insufficient aeration of the wort, low concentration of yeast in the inoculum, poor yeast growth due to insufficient nutrients, unsuitably high or low fermentation temperatures, excessive yeast growth, and the like. Some fermentation processes are characterized by a low initial fermentation rate (caused by poor initial yeast growth or inadequate inoculum) and an increase in fermentation over time.

Within the brewing industry, there is considerable interest in increasing the rate of fermentation. Increased fermentation rates not only reduce fermentation time, but also reduce the incidence of brewing failures due to contamination by microorganisms, which may result in an unacceptably poor quality product.

Fermentation may be enhanced by a variety of known means. For example, U.S. Pat. Nos. 899,756; 1,041,298; and 2,121,458 teach that aeration of the wort/yeast solution can assist in the growth of yeast to promote fermentation. Belgium Patent 1010885A3 teaches that the aeration of the wort/yeast suspension may be achieved by using a porous membrane. However, it is believed that aerating the wort/yeast solution may contribute to the production of staling precursors (Uchida, et al., *J. Am. Soc. Brew. Chem.* 58(1):30-37 (2000)). Another approach to enhancing fermentation is by adding zinc to the yeast/wort solution as disclosed in U.S. Pat. Nos. 3,164,472 and 4,840,802.

Another way in which the fermentation rate may be increased is by increasing the pitching rate. Adequate pitching reduces lag time and reduces the likelihood that a bacterial contaminant will become established. The pitching rate may be increased by increasing the number of yeast cells added to the wort, or by using a yeast starter culture.

A starter culture may be made by first inoculating a smaller volume of wort with an active yeast followed by vigorous aeration/agitation which allows for the concentration of active yeast cells to increase before pitching the starter culture into a larger volume of wort.

Commonly, wort is pitched with yeast derived from a previous fermentation. Generally, this yeast has experienced anaerobic conditions during fermentation. Before fermentation can occur, the yeast which is harvested from the anaerobic beer environment and is used to pitch the wort must be supplied oxygen in order to synthesize essential lipid components, including sterols and unsaturated fatty acids. Synthesis of these lipids requires molecular oxygen and a carbohydrate source, such as glycogen, stored in the yeast cells.

A conventional approach to insuring sufficient oxygen for yeast to synthesize lipids has been to oxygenate the wort. However, the level of oxygen in the wort must be controlled to avoid slow fermentation and subsequent flavor changes caused by sub-optimal concentrations of oxygen, and reduced ethanol yields and flavor changes that result from excessive yeast growth and metabolic changes caused by high levels of oxygen.

Another approach to enhancing fermentation rates is to pitch wort containing no oxygen or reduced oxygen with a starter culture of yeast prepared by allowing yeast to grow with exposure to oxygen in a smaller volume of wort for several hours. This method allows control of fermentation by controlling the pitching rate.

UK Patent Application GB 2 197 341 discloses a method of fermenting wort in which the pitching yeast is first suspended in water and exposed to oxygen for a period of time until the yeast reaches its maximum rate of oxygen consumption. The yeast is then used to pitch oxygen-free wort.

There remains a need in the art for improved methods of enhancing fermentation.

BRIEF SUMMARY OF THE INVENTION

The present invention includes a method of aerating yeast for use in fermentation comprising the steps of:

(a) suspending yeast in an aqueous solution comprising a fermentable sugar in a concentration sufficient to give gravity in the range of from about 2 to about 25 degrees Plato and zinc in a concentration effective to promote yeast health and performance in subsequent fermentation; and (b) aerating the suspension for a period of time and under conditions suitable to allow sterol and unsaturated fatty acid biosynthesis.

Another aspect of the invention is a method of fermenting a fermentable medium comprising the steps of:

(a) suspending yeast in an aqueous solution comprising a fermentable sugar in a concentration sufficient to give gravity in the range of from about 2 to about 25 degrees Plato and zinc in a concentration effective to promote yeast health and performance in subsequent fermentation;

(b) aerating the suspension for a period of time and under conditions suitable to allow sterol and unsaturated fatty acid biosynthesis;

(c) transferring the yeast of step (b) to a suitable volume of fermentation medium having a gravity comparable to the gravity of the solution of step (a); and (d) allowing fermentation to occur under suitable fermentation conditions.

A still further aspect of the invention provides for a fermented beverage, such as beer, and a fermented food, such as kefir, made by using a yeast that has been treated according to the foregoing methods.

It is an object of the present invention to provide an improved method for aerating yeast.

It is an advantage of the invention that nonaerated wort may be used as the fermentation medium, which may reduce formation of staling precursors associated with the use of aerated wort during fermentation.

DETAILED DESCRIPTION OF THE INVENTION

The present invention provides an economical and convenient method of aerating yeast prior to pitching. Aerating yeast prior to pitching allows the yeast cells to obtain sufficient oxygen to synthesize sterols and unsaturated fatty acids, which are needed for cell growth during the fermentation process. By oxygenating the yeast rather than the wort, greater consistency of the final product may be attained with minimal exposure of the wort to molecular oxygen.

In the method of the invention, yeast is aerated in an aqueous sugar solution prior to the addition of fermentation medium. In the examples below, a diluted liquid adjunct was employed as the fermentable carbon source. By a "diluted liquid adjunct" it is meant a solution of fermentable carbohydrate comprising, but not limited to, dextrose, maltose, and maltotriose. Preferably, it is a dilution of an 85% w/w solution of 77% w/w fermentable carbohydrate comprising 31% w/w dextrose, 36% w/w maltose and 10% w/w maltotriose. However, any aqueous solution containing a simple fermentable sugar or complex mixture of fermentable sugars and nonfermentable carbohydrate derived from the conversion of starch or any other polysaccharide may be used. Other suitable fermentable sugars that may be employed in the practice of the invention include fructose, sucrose, raffinose, trehalose, melibiose, galactose, and lactose depending on the yeast strain used. Preferably, the aqueous sugar solution is substantially free of organic compounds known to be involved in beer staling.

In the examples below, the aqueous sugar solutions used to aerate yeast comprised liquid adjunct at a concentration of about the same as the wort that the yeast will subsequently be added to. It is reasonably expected that sugar concentrations in the range of from about 2% w/w to about 25% w/w would yield acceptable results. In other words, the aqueous sugar solution and wort solution must be compatible with the osmotolerance of the yeast.

The time required to aerate yeast will depend upon the rate at which oxygen or air is delivered into the solution and the yeast's maximum oxygen uptake rate (OUR). When air/oxygen is being delivered at a rate in excess of the yeast's maximum OUR, the amount of aeration is dependent strictly on the yeast's exposure time. After the yeast has aerated sufficiently, nonoxygenated wort having approximately the same specific gravity as the original yeast/sugar solution is added to the yeast or the yeast is added to the wort. Preferably, the delivery of air/oxygen into the yeast/sugar solution should be above the maximum OUR of the yeast.

One of ordinary skill in the art will appreciate that one could also add aerated yeast to aerated wort, which could be expected to further enhance fermentation rates relative to aerated wort pitched with nonaerated yeast and relative to nonaerated wort pitched with aerated yeast.

Following pitching, fermentation is allowed to proceed using standard fermentation conditions and a standard fermentation vessel. Fermentation is completed in a shorter time than conventional fermentation methods, in which aerated wort is pitched with non-aerated yeast slurry.

In addition to enhancing the fermentation rate, the method of the invention avoids problems associated with aerating the yeast after transfer to wort. Such problems include formation of staling precursors and foaming. The present invention also allows greater flexibility in the brewing process.

Yeast is normally used to inoculate ("pitch") a fermentation medium or wort at a rate in the range of from about 10 million to about 20 million cells/ml wort. Some brewers use about one million cells per ml, per degree Plato (Plato is the w/w % of fermentable carbohydrate). For example, for a 14 degree Plato wort, one would pitch at a rate of 14 million yeast cells/ml. With the present invention, yeast that is used in the fermentation is first suspended in a volume of an aqueous sugar solution that is in the range of from about 5% to about 20% of the volume of the final fermentation.

The sugar/yeast solution is adjusted to the desired original gravity (degrees Plato) of wort, but could be used in a concentration of from about 2 to about 25 degrees Plato. In a typical example, if one were fermenting a 14 degrees Plato wort, the sugar/yeast solution would be adjusted to 14 degrees Plato prior to aeration of the sugar/yeast solution. If the gravity of the sugar solution is different from that of the wort, then the wort must be adjusted accordingly to achieve the desired original gravity for the sugar and wort solutions combined.

The addition of zinc to the yeast/sugar solution promotes improved yeast health and performance in the subsequent fermentation. Preferably, the aqueous sugar solution includes zinc in a concentration sufficient to promote yeast health and to protect against or reduce stress to cells under nitrogen starvation conditions. As shown in the examples below, the zinc concentration must be greater than one times the w/v percent normally used in the wort in order to increase the fermentation rate, relative to an aerated yeast preparation containing no added zinc. Zinc salts are preferably added to the sugar solution at a level that is 1-50 times the concentration of what would normally be added to the wort. The optimum for yeast health appears to be around five to ten times the concentration of zinc normally used in the wort, although lower concentrations still confer a protective effect, and higher concentrations do not appear to have any adverse effects.

We have conducted considerable research to evaluate the effects of the length and rate of aeration, as well as the differential effects of using air vs. pure oxygen in yeast. Typically, the yeast aerated in a sugar solution for from about 8 hours up to about 21 hours exhibit optimal yeast performance in subsequent fermentations. The optimal aeration time may vary according to the aeration rate or the source of oxygen (e.g., air or pure oxygen), but typically the aeration/oxygenation rate is kept above the maximum OUR of the yeast. When this is done, the time of exposure is the most critical factor.

The pH of the yeast/sugar solution may be adjusted so that it is at least 3.0, preferably greater than 6.0, and most preferably about 7.0. Aeration in a sugar solution having a pH of about 6.0 is correlated with reduced yeast cell death during aeration and enhanced fermentation rates in subsequent fermentation.

Yeast aeration was conducted at normal fermentation temperatures (about 60° F.) because it was expected that yeast would use the oxygen supplied to synthesize sterols and unsaturated fatty acids optimally at temperatures near their normal fermentation temperature. However, it is expected that aeration can be conducted at temperatures in the range of from about 32° F. to about 80° F., depending on the type of yeast and the type of fermentation.

In the examples below, wort was used as the fermentable medium. However, it is reasonably expected that other fermentation media would be equally suitable in the practice of the invention.

In the examples below, brewer's lager yeast was employed. Other suitable yeasts include, without limitation, ale yeast, wine yeast, distiller's yeast, baker's yeast, champagne yeast, cider-making yeast, Kluveromyces yeast, etc.

Following oxygenation, the yeast may be used for pitching. Fermentation is allowed to proceed using standard fermentation conditions. Depending on the brewer's objective, the yeast may be used to pitch aerated or unaerated wort.

If the primary objective is affecting or controlling flavor profiles or to prevent formation of staling precursors, nonaerated wort should be used in the fermentation.

It is envisioned that the method of the invention may be used to obtain high fermentation rates by using aerated yeast to pitch aerated wort. Typically, fermentation may be completed in a shorter time using yeast aerated by the method of the invention than by conventional fermentation methods, in which aerated wort is pitched with non-aerated yeast.

In addition to pitching and fermentation, yeast aerated by the method of the invention may be used in other aspects of the brewing process, including krauesening, lagering, or any other application in which yeast is generally used.

It is envisioned that the present invention will be particularly useful in the brewing industry. However, it is not intended that the method be limited to wort fermentations. It is reasonably expected that yeast aerated by the method of the invention would also be suitable in other yeast fermentation industries, including the wine and alcohol production industries.

The following nonlimiting examples are intended to be purely illustrative.

EXAMPLES

Yeast Aeration

Brewers' lager yeast was aerated in liquid adjunct (17° Plato after the yeast addition) supplemented with 0.25 ppm zinc, which was five times the concentration of zinc supplement normally added to the wort for subsequent fermentations. The yeast concentration was at $10^8$ cells/ml of the final sugar solution. The yeast was aerated at 60° F. with an air injection rate of 1.5 standard cubic feet per hour (scfh) for three, seven, fourteen, or twenty-one hours.

Effect of Length of Yeast Aeration on Days to End of Fermentation (EOF)

Standard fermentations were conducted in nonaerated wort having a gravity of 16° Plato by pitching the wort with yeast aerated for various lengths of time. The pitching rate was $10^7$ yeast cells/ml of wort. The specific gravity was monitored over time to determine the number of days to the end of fermentation.

The results are shown in Table 1.

TABLE 1

Time to End of fermentation (EOF) Using Yeast
That Has Been Aerated for Different Lengths of Time

| Length of aeration (h) | Days to EOF |
|---|---|
| 3 | 8.1 |
| 7 | 7.3 |
| 14 | 6.5 |
| 21 | 5.8 |
| Aerated wort control | 7.0 |

The results show that the time to EOF varies inversely to the length of yeast aeration. Fermentations using yeast aerated for seven hours give an EOF comparable to aerated wort pitched with nonaerated yeast. Yeast aerated for longer periods of time reduce the EOF considerably.

Effect of Zinc on End of Fermentation Times

To determine the effect of zinc concentration in aerated yeast on EOF times, yeast was supplemented with varying concentrations of zinc and aerated for 21 hours as described above. The yeast was used in subsequent fermentations, as described above. The results are shown in Table 2.

TABLE 2

Effect of Zinc Addition on Required Time to End of
Fermentation (EOF) Using Yeast Aerated for 21 Hours

| Zinc addition level | Days to end-of-fermentation (EOF) |
|---|---|
| None | 6.2 |
| 0.05 mg/l | 6.2 |
| 0.25 mg/l | 5.4 |
| 0.50 mg/l | 5.5 |
| 2.00 mg/l | 5.4 |
| Aerated wort control (no zinc addition and non-aerated yeast) | 6.9 |

The above results indicate that the addition of greater than 0.05 mg/l zinc (0.05 mg/l is normally added to the wort) to the yeast aeration is required to give an improvement over aerating yeast with no zinc addition.

Effect of Oxygen Source on Aerated Yeast

Yeast was aerated using air or oxygen for various lengths of time and at various rates. The yeast was used in subsequent fermentations. The effect of air or oxygen on EOF is shown in Table 3.

TABLE 3

Yeast Aeration Using Air vs. Oxygen for Various Lengths
of Times and Different Injection Rates and the Effect on
Time to End of Fermentation (EOF)

| Gas | Injection rate (SCFH) | Length of aeration (h) | Days to end of fermentation |
|---|---|---|---|
| Air | 1.5 | 21 | 5.4 |
| $O_2$ | 0.32 | 21 | 5.8 |
| $O_2$ | 1.5 | 2.5 | 6.9 |
| $O_2$ | 1.5 | 4.5* | 6.8 |
| $O_2$ | 1.5 | 6.5 | 6.6 |
| Aerated wort control | Not applicable | Not applicable | 6.1 |

*indicates the time (4.5 hours) at which the yeast oxygenation using $O_2$ at 1.5 scfh is equivalent (for fermentation effect) to yeast aeration using air at 1.5 scfh over a 21 hour aeration.

The results presented in Table 3 indicate that the length of time of aeration is more critical than the source of oxygen employed or the rate of injection, provided that the injection rate exceeds the yeast's maximum oxygen uptake rate (OUR). Yeast aerated using $O_2$ at higher rates for a shorter period of time can not replace yeast aerated with air for a longer time because the OUR is at a maximum in both instances, and it is the length of aeration that is important.

Effect of Air Injection Rate on Fermentations

The rate of air injection during a 10 hour yeast aeration was varied and its effect on EOF was determined. The results are shown below in Table 4.

TABLE 4

The Effect of Various Yeast Aeration Air Injection Rates
on the Time to the End of Fermentation (EOF)

| Injection Rate (SCFH) | Days to End-of-fermentation |
|---|---|
| 1.5 | 6 |
| 3 | 6 |
| 6 | 5.9 |
| Aerated wort control | 6.5 |

The above results show that doubling and quadrupling the air injection over a 10 hour aeration time did not improve fermentation.

Effect of pH on Fermentation Time and Cell Survival

Yeast was aerated with air at 1.5 scfh for 21 hours in the presence of 0.25 mg/l zinc in liquid adjunct in which the pH was adjusted, as shown below in Table 5.

TABLE 5

Effect of pH Adjustment during Yeast Aeration on Yeast
Viability and the Time to End of Fermentation (EOF)

| pH | % Dead cells after aeration | Days to End-of-Fermentation |
|---|---|---|
| <4.0 | 53.7 | 5.8 |
| 5.4 | 20 | 4.9 |
| 6.9 | 5.4 | 4.9 |
| Wort pH | 0.4 | 5.9 |

The above results show that increasing the pH of the yeast/sugar aeration solution to a pH of greater than 4.0 prior to aeration improves cell viability at the end of aeration and improves fermentation performance.

The present invention is not limited to the exemplified embodiments, but is intended to encompass all such modification and variation as come within the scope of the following claims.

We claim:

1. A method of enhancing yeast fermentation of wort, the method comprising the steps of:
    (a) suspending yeast in a wort-free aqueous solution comprising liquid adjunct in an amount sufficient to give a specific gravity in the range of from about 2 to about 25 degrees Plato, wherein the liquid adjunct comprises a cereal sugar;
    (b) aerating the yeast suspension for a period of time with a gas comprising oxygen to allow oxygen uptake by the yeast, wherein the gas is delivered above a maximum oxygen uptake rate of the yeast and wherein the period of time is 8 hours up to about 21 hours;
    (c) adding zinc to the yeast suspension of step (b);
    (d) transferring the yeast suspension of step (b) to a suitable volume of nonaerated wort having a specific gravity comparable to the specific gravity of the solution of step (a); and
    (e) allowing fermentation to occur under suitable fermentation conditions to produce beer.

2. The method of claim 1 wherein the liquid adjunct comprises maltose.

3. The method of claim 1 wherein the liquid adjunct comprises dextrose, maltose and maltotriose.

4. A method for fermenting wort, the method comprising:
    (a) suspending yeast in a wort-free aqueous solution comprising liquid adjunct in an amount sufficient to give a specific gravity in the range of from about 2 to about 25 degrees Plato wherein the liquid adjunct comprises a cereal sugar;
    (b) aerating the yeast suspension for a period of time with a gas comprising oxygen to allow oxygen uptake by the yeast, wherein the gas is delivered above a maximum oxygen uptake rate of the yeast and wherein the period of time is 8 hours up to about 21 hours;
    (c) adding zinc to the yeast suspension of step (b);
    (d) transferring the yeast suspension of step (b) to a suitable volume of non-aerated wort having a specific gravity comparable to the specific gravity of the solution of step (a);
    (e) allowing fermentation of the wort to occur to produce beer; and
    (f) monitoring the wort for an end of fermentation, wherein the end of fermentation is indicated by a pre-determined decline in specific gravity,
    wherein the end of fermentation is reached in a shorter time than a fermentation method wherein aerated wort is pitched with a non-aerated yeast slurry.

5. The method of claim 4, wherein the yeast is brewer's yeast.

6. The method of claim 4 wherein the liquid adjunct comprises maltose.

7. The method of claim 4 wherein the liquid adjunct comprises dextrose, maltose and maltotriose.

* * * * *